United States Patent [19]

Shanks

[11] Patent Number: 4,588,129

[45] Date of Patent: May 13, 1986

[54] NEBULIZER

[75] Inventor: Thomas P. Shanks, Temecula, Calif.

[73] Assignee: Hudson Oxygen Therapy Sales Company, Temecula, Calif.

[21] Appl. No.: 529,511

[22] Filed: Sep. 6, 1983

[51] Int. Cl.[4] ............................................. A61M 11/00
[52] U.S. Cl. ................................. 239/338; 128/200.18; 239/370
[58] Field of Search ............................... 239/338, 370; 128/200.14, 200.18, 200.21

[56] References Cited

U.S. PATENT DOCUMENTS

| | | | |
|---|---|---|---|
| 1,150,238 | 8/1915 | Winbray | 239/338 |
| 2,840,417 | 6/1958 | Dorsak et al. | 239/338 |
| 3,353,536 | 11/1967 | Bird et al. | 128/194 |
| 3,522,806 | 4/1970 | Szekely | 239/338 X |
| 3,584,621 | 6/1971 | Bird et al. | 128/145.5 |
| 3,744,722 | 7/1973 | Burns | 239/338 |
| 3,762,409 | 10/1973 | Lester | 128/200.14 |
| 3,838,686 | 10/1974 | Szekely | 239/338 |
| 4,333,450 | 6/1982 | Lester | 128/200.14 |

Primary Examiner—Jeffrey V. Nase
Attorney, Agent, or Firm—Seiler, Quirk & Tratos

[57] ABSTRACT

An improved nebulizer for directing an aerosol from a spray orifice toward an outlet pipe against a target comprises a convex target surface substantially enlarged relative to the diameter of the spray orifice and a cylindrical hood coaxially surrounding said target having a single open port coaxial with said spray orifice, the spray orifice including means for forming an inverted aerosol cone all of which first impinges against the target, and whereby substantially all of the aerosol must exit from the cavity through the single open hood port.

7 Claims, 6 Drawing Figures

NEBULIZER

BACKGROUND OF THE INVENTION

Nebulizers for producing aerosol for use in respiratory therapy are well known. A popular and efficient nebulizer incorporates a vertical air nozzle having a lower end into which gas is directed and an upper gas exit orifice, the air nozzle being surrounded by a concentric aspirator cap. A bowl forming a reservoir for holding water and/or medication communicates with channels extending between the nozzle and aspirator cap, the latter having a spray orifice at the upper end, also concentric with the gas orifice. An impingement target, preferably convex, is located directly above the spray orifice of the aspirator cap. Aerosol created by the device impinges against the target surface and then passes through an outlet pipe. Such a nebulizer is shown in U.S. Pat. No. 3,826,255 and another similar device in U.S. Pat. No. 3,762,409. Although such nebulizers produce an adequate aerosol, the particle size distribution is not entirely satisfactory. Particularly, in the latter device, a substantial percentage of particles passing through the outlet pipe have a particle size of 10 microns or greater. The present invention is directed to a device which generates an aerosol having a particle size of less than 10 microns, preferably a substantial amount of particles in the 1–5 micron range, and more preferably a majority of the particles in the 1–3 micron size interval.

SUMMARY OF THE INVENTION

In the present nebulizer apparatus, concentric air and spray nozzles are utilized in cooperation with a convex impingement surface or target surrounded by a hood, both the hood and target being concentric with the nozzle orifices. The size of the target, its distance from the spray nozzle, and the location of the single hood opening relative to the spray nozzle and baffle all cooperate to achieve an aerosol having an improved particle size distribution.

DETAILED DESCRIPTION OF THE INVENTION

Figure 1:
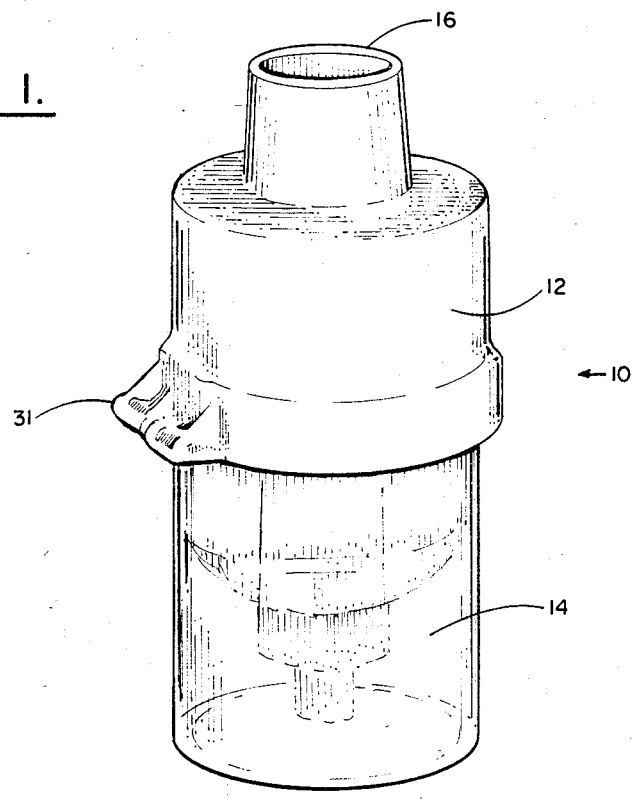
FIG. 1 is a side view of the assembled nebulizer of the invention.
Figure 2:
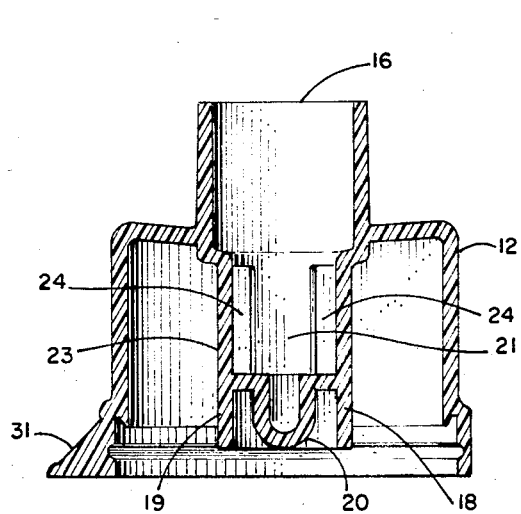
FIG. 2 is a sectional elevation of the lid portion of the nebulizer.
Figure 3:
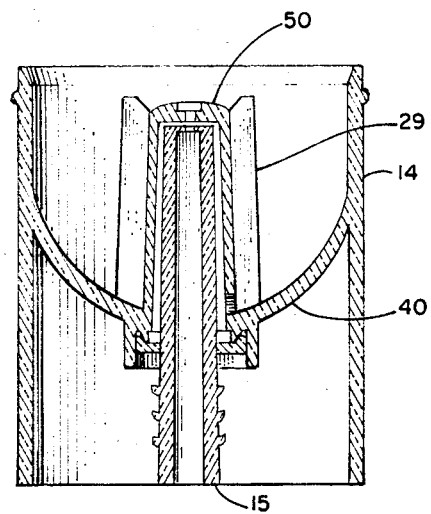
FIG. 3 is a sectional elevation of the jar portion of the nebulizer.
Figure 4:
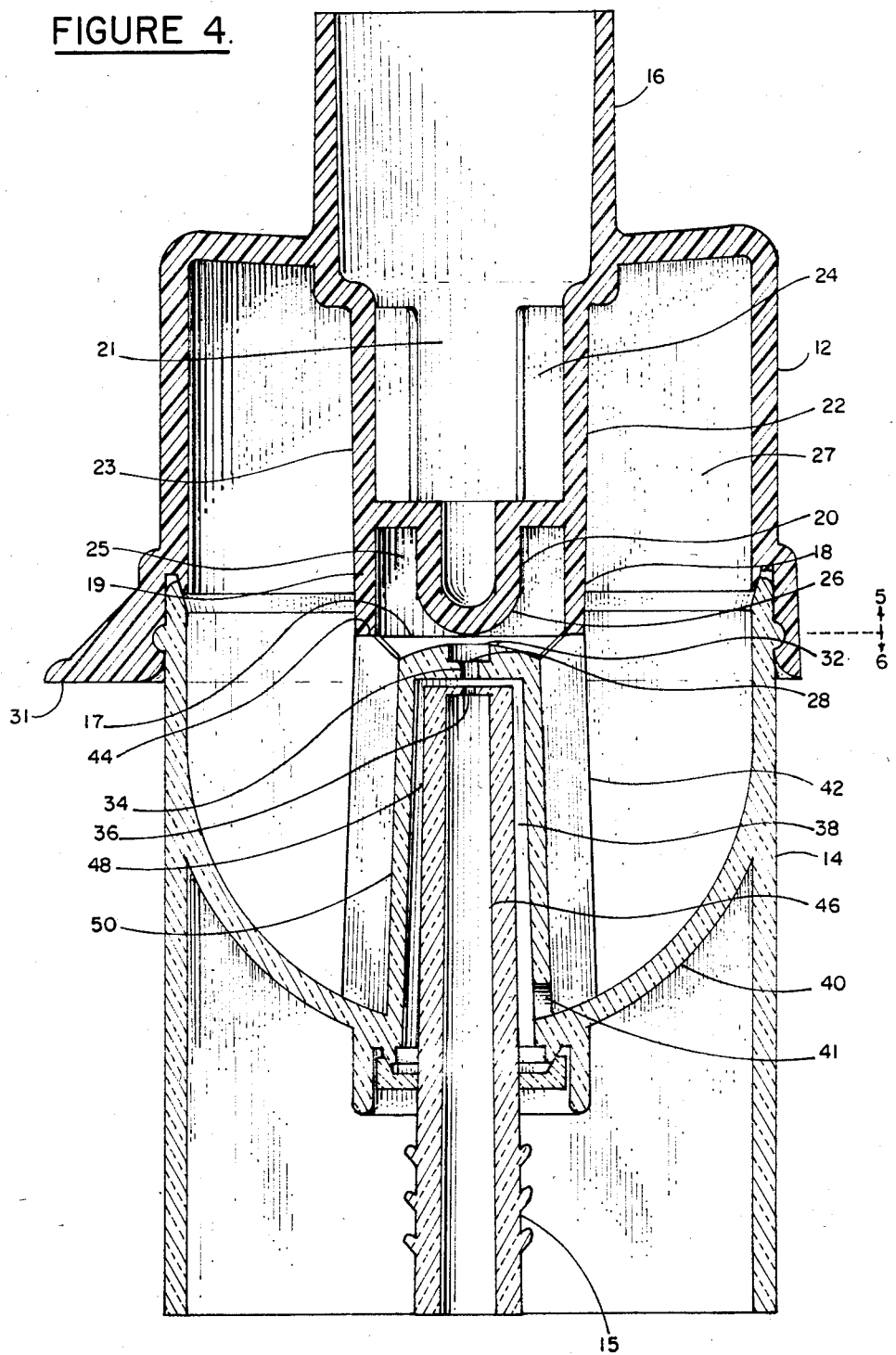
FIG. 4 is a sectional elevation of the assembled lid and jar portions illustrating the important physical relationships of the components thereof.

Observing now the drawings, there is illustrated the improved nebulizer 10 of the invention. In the preferred embodiment, the nebulizer comprises a lid portion 12 and a jar portion 14. The assembled components are shown in FIGS. 1 and 4. The lid portion 12 includes an aerosol outlet pipe 16, target 20, preferably coaxial with outlet pipe 16, and a hood 19 formed by an annular skirt 18 extending around the target. The hood and target are supported by members 21, 22 and 23. The number of support members is not critical, so long as there are openings or ports 24 between the support members to allow aerosol to pass from the interior of the lid into outlet pipe 16. The jar portion 14 includes a bowl 40 for holding a supply of water used to create the aerosol generated by the apparatus, and a nozzle assembly 29 as will be more fully described hereinafter.

Observing the more detailed structure shown in FIG. 4, the nozzle assembly for generating the aerosol includes a gas inlet pipe 15 accessible at the bottom of the jar 14 to which a hose is attached for directing gas, normally an oxygen enriched gaseous mixture, into gas nozzle 48. The interior of the gas nozzle is hollow, forming a channel 46 for directing the gas to gas orifice 36. An aspirator cap 50 is coaxially secured relative to gas nozzle 48, the two components separated by a water channel 38. The latter may extend entirely around the outer wall of the gas nozzle and inner wall of the aspirator cap, or may actually comprise a plurality of channels. Water channel 38 communicates adjacent its lower end with water inlet passageway 41, which opens to the enlarged cavity of the jar, so that water placed in the jar and held in bowl 40 passes directly into water channel 38 via the passageway. At upper end of aspirator cap 50 is a port 34 having at its upper lip spray orifice 28 which directs an aerosol to surface 26 of target 20.

Water channel 38 communicates with both the gas orifice 36 and spray channel 34. Water or other liquid to be used in creating the aerosol is held in bowl 40. Gas is introduced into gas nozzle 48 and because of the lower pressure in spray channel 34 due to its increased diameter relative to gas orifice 36, the water is drawn upwardly into the water channel via water inlet passageway 41, where it meets with gas from gas orifice 36. A similar relationship of the aspirator cap and the gas nozzle including water channel 38 is also shown generally in U.S. Pat. No. 3,826,255, the pertinent portions thereof being incorporated herein by reference.

A most important feature of the nebulizer of the invention is the relationship of the spray orifice to the target surface and the hood. The target surface 26 is convex and the center or apex of the surface is coaxial with spray orifice 28 and gas orifice 36. The distance between the target surface and the spray orifice is preferably such that all of the aerosol blown from the orifice impinges on the target surface. To meet that preferred requirement, the diameter of the target surface must be substantially greater than the diameter of the spray nozzle. The specific diameter or radius of the convex target surface is not critical, so long as all of the aerosol impinges against it. Thus, the enlarged target must present a target surface of size sufficient to intercept all of the aerosol flowing from the spray nozzle. Although the target could be placed very close to the spray nozzle orifice, where it is too close, a back splash is created by the impinging particles rebounding against the aerosol flow. To avoid such a problem, the nearest point or apex of the target is spaced from the center of the spray nozzle orifice at least a distance equal to the spray nozzle diameter. The diameter of the spray nozzle orifice is preferably between about 0.025 and 0.035 inch with 0.031±0.002 inch most preferred. At normal gas delivery pressure of about 50 psi, the aerosol delivered from the spray nozzle will be in the form of an inverted cone. The velocity of the aerosol blown from the spray nozzle will be greatest nearest the orifice, and thus the closer the target is to the nozzle orifice, the more efficient it will be in fracturing large particles of the aerosol. If the target is too far away from the nozzle, particle velocity is decreased as is the concomitant force of a given particle impinging against the target surface, thereby reducing particle fracture efficiency. A further problem is that as the distance between the target and nozzle increases, so does the diameter of the inverted aerosol cone, thereby requiring a greater target surface diameter to intercept all of the aerosol particles. According to the invention, improved results are achieved where the distance between the center of the spray nozzle orifice and the apex of the convex target surface is between about 1 and about 2 times the diameter of the spray nozzle orifice, and preferably between about 1 and 1½ times.

In another embodiment of the invention as shown, a second spray orifice 32 is used in cooperation with spray nozzle orifice 28 for ensuring that the inverted aerosol spray cone diameter is not greater than the target diameter. For this purpose, such a second orifice should have a diameter and distance from the spray orifice such that the outer limit of a cone created by extending a straight line from the edge of the spray nozzle orifice 28 to the edge of the second spray orifice does not have a diameter greater than the effective or exposed surface diameter. Instead, the outer cone limit must intersect or make contact with the exposed target surface thereby avoiding any overspray of aerosol into the nebulizer cavity without first impinging against the target surface. Thus, the second spray orifice acts to limit or restrict the dimension of the aerosol spray cone and ensure its impingement against the target surface within a relatively short distance from the spray nozzle orifice when particle velocity is greatest. The center of such a second spray orifice, as shown, is preferably spaced from the center of the target surface about ¼ to ¾ of the distance that the spray nozzle orifice is separated from the target surface, and more preferably about ⅓ to ½ of the distance. Again, the diameter of the second spray orifice is only critical in that it must restrict or trim the aerosol cone to fit within the effective target surface area. Preferably, with the spray nozzle orifice dimensions and target distances given above, second spray orifice diameters between 2 and 3 times the spray nozzle orifice diameter are preferred.

A further important feature is a hood 19, preferably annular, extending and concentric with the target. The hood comprises a skirt 18 having a lower or bottom edge 44 which lies along a single plane that intersects target surface 26, or extends slightly beyond the target surface in the direction of the nozzle assembly. More preferably, the bottom edge of the skirt lies along a plane which touches the apex or center of the convex baffle surface 26 as illustrated in FIG. 4. Between the skirt and the target is a completely enclosed hood chamber 25. The only opening in the hood is the enlarged open port 17 formed by the bottom edge 44 of skirt 18. The important feature of the hood is to provide a chamber in which the distance between the target surface and the inner skirt wall will not allow larger particles to pass out of the chamber with the gas. Instead, such large particles are directed against and collect on the interior hood surface to form droplets which are returned gravitationally to the liquid supply in bowl 40. The smaller aerosol particles up to about 10 microns, are forced downwardly along with the gas flow through hood port 17 into the main inlet chamber 27, through port 24 and out of aerosol outlet pipe 16.

Figure 5:
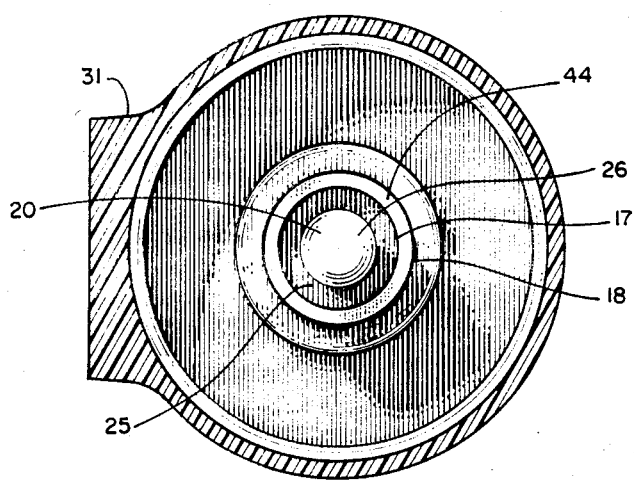
FIG. 5 is a sectional view taken along lines 5—5 of FIG. 4.
Figure 6:
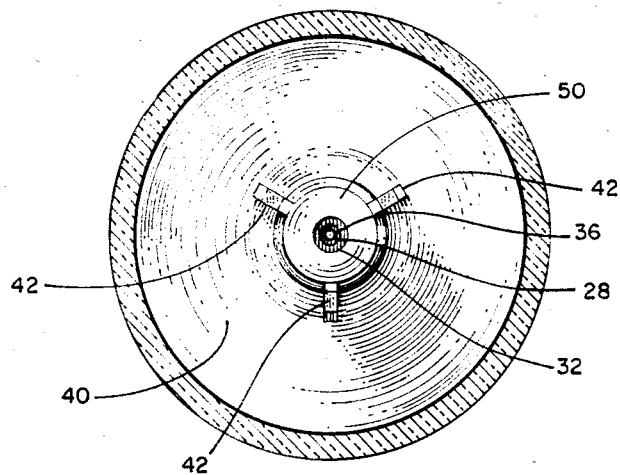
FIG. 6 is a view taken along lines 6—6 of FIG. 4.

In order to maintain the preferred distances between the target surface and spray nozzle orifice, a plurality of supports 42 are conveniently used which have an upper surface for abutting against the bottom edge 44 of skirt 18 when lid 12 and jar 14 are fully assembled and secured together. The location of such supports is illustrated in FIG. 6, with support 42 extending outwardly from aspirator cap 50, the relationship of gas orifice 36, spray nozzle orifice 28 and second spray orifice 32 being also shown. The relationship of surface 26 of target 20 to skirt 18 is also illustrated in FIG. 5, along with chamber 25 and open port 17 of the hood.

In a specific apparatus as described herein, a superior aerosol may be achieved utilizing a device having a nominal gas orifice diameter of 0.021 inch, spray nozzle orifice diameter of 0.031 inch, second spray orifice diameter of 0.095 inch, and a distance from the center of the spray nozzle orifice to the apex of the target surface of 0.0375 inch and the distance between the center of the second spray orifice and the target is 0.0125 inch. At a flow rate of 7 liters per minute, the nebulizer achieved an aerosol in which substantially all the particles were 10 microns or less, 98% of the particles were between 1 and 5 microns and 61% use between 1 and 3 microns. The results were achieved by analyzing an aerosol from the outlet pipe dispersed into a Royco Model 225 particle monitoring instrument using forward scattering techniques to measure the size of the particles.

I claim:

1. In a nebulizer having a spray orifice means for directing an aerosol upwardly therefrom to an otulet pipe, and a target between said spray orifice means and said outlet pipe against which said aerosol is directed, the improvement comprising: said target having a convex surface forming an impingement surface facing said spray orifice means and a hood having an annular skirt with a bottom edge forming a single circular portion, the hood being otherwise enclosed, the center of said convex surface being substantially coaxial with said spray orifice means and centered relative to said circular port wherein said spray orifice means is circular and said convex surface has a diameter greater than the diameter of said orifice, and the diameter of said circular port is greater than the diameter of said target, said spray orifice means comprising a spray nozzle orifice and a second spray orifice, said spray nozzle orifice being spaced further from said target than said second spray orifice, the distance between said spray nozzle orifice and the center of said target surface being at least as great as the diameter of said spray nozzle orifice, wherein the diameter of said second spray orifice is greater than the diameter of said spray nozzle orifice and adapted to limit the size of an aerosol cone sprayed from said spray nozzle orifice and wherein an outer limit of a cone created by extending a straight line from the edge of said spray nozzle orifice and the edge of said second spray orifice must intersect said target impingement surface whereby all of said aerosol cone impinges said target surface.

2. The nebulizer of claim 1 wherein the closest distance from said second spray orifice and said target is less than the diameter of said spray nozzle orifice.

3. The nebulizer of claim 2 wherein the distance between said spray nozzle orifice and said target is between about 1 and about 2 times the diameter of said spray nozzle orifice.

4. The nebulizer of claim 2 wherein the distance between said spray nozzle orifice and said target is between about 1 and about 1.5 times the diameter of said spray nozzle orifice.

5. The nebulizer of claim 4 wherein the diameter of said spray nozzle orifice is between about 0.025 and about 0.035 inch.

6. The nebulizer of claim 5 wherein said second spray orifice is spaced from the target surface about ⅓ to ½ of the distance that the spray nozzle orifice is spaced therefrom.

7. The nebulizer of claim 1 wherein the apex of said convex surface and said bottom edge of the hood skirt lie in said same single plane.

* * * * *